United States Patent [19]

Melville

[11] 4,394,127

[45] * Jul. 19, 1983

[54] METHOD OF DEPOSITING PERFUME AND COMPOSITIONS THEREFOR

[75] Inventor: James B. Melville, Wirral, England

[73] Assignee: Lever Brothers Company, New York, N.Y.

[ * ] Notice: The portion of the term of this patent subsequent to Apr. 27, 1999, has been disclaimed.

[21] Appl. No.: 230,484

[22] Filed: Feb. 2, 1981

[30] Foreign Application Priority Data

Feb. 7, 1980 [GB] United Kingdom ................. 8004106
Feb. 7, 1980 [GB] United Kingdom ................. 8004107
Feb. 7, 1980 [GB] United Kingdom ................. 8004108

[51] Int. Cl.$^3$ .......................... A61K 7/46; B08B 3/00; C11D 3/50; C11D 17/01

[52] U.S. Cl. .......................................... 8/137; 252/90; 252/173; 252/174; 252/174.11; 252/174.13; 252/522 A; 252/525; 252/544

[58] Field of Search ...................... 252/174.11, 174.13, 252/174, 90, 522 A, 525, 544; 8/137

[56] References Cited

U.S. PATENT DOCUMENTS

| | | | |
|---|---|---|---|
| 3,853,779 | 12/1974 | Inamorato | 252/110 |
| 4,141,841 | 2/1979 | McDanald | 252/8.8 |
| 4,151,097 | 4/1979 | Nelson | 252/8.6 |
| 4,152,272 | 5/1979 | Young | 252/8.8 |
| 4,292,035 | 9/1981 | Battrell | 8/137 |
| 4,294,710 | 10/1981 | Hardy | 252/8.8 |

FOREIGN PATENT DOCUMENTS

| | | | |
|---|---|---|---|
| 1204123 | 9/1970 | United Kingdom | 252/106 |
| 1367261 | 9/1974 | United Kingdom | 252/8.8 |
| 1514276 | 6/1978 | United Kingdom | 252/8.8 |
| 1544863 | 4/1979 | United Kingdom | 252/8.8 |
| 1560640 | 2/1980 | United Kingdom | 252/174.11 |

*Primary Examiner*—Dennis L. Albrecht
*Attorney, Agent, or Firm*—Milton L. Honig; James J. Farrell

[57] ABSTRACT

A method of cleaning and depositing perfumes on a surface comprises contacting the surface with a liquor containing a surfactant having a size of 0.1 to 2000 microns and particles comprising a perfume and a water dispersible amine. The surfaces to be treated may be fabrics or hard surfaces. Preferred amines are the primary and tertiary alkyl amines, where one alkyl group has from 8 to 22 carbon atoms. The particles may be made by forming a liquid mixture of the amine and the perfume, and then solidifying and forming into particles. The particles may be incorporated in a variety of products including fabric washing powders and liquid, was-addable solids or liquids, and hard surface cleaning powders and liquids.

6 Claims, No Drawings

METHOD OF DEPOSITING PERFUME AND COMPOSITIONS THEREFOR

TECHNICAL FIELD

This invention relates to a method of cleaning surfaces and depositing perfumes thereon. It also relates to compositions for carrying out such a method and to methods of making such compositions. The surfaces which can be treated by the method of the invention include fabrics such as cotton, wool, polyacrylic, polyester and polyamide fibres and hard surfaces such as ceramic, plastics material laminate, metal and glass. The methods are applicable to the treatment of such surfaces both by hand and by machine, such as the machine washing of fabrics.

BACKGROUND ART

It is known to include perfumes in detergent compositions to provide a pleasant after-smell on the treated surfaces. It is desirable to have the perfume component of a detergent composition used efficiently because it is a relatively high cost component. In use, the perfume will be often present in the treatment liquid at a relatively low concentration.

It has been proposed in British Pat. 1,544,863 to incorporate perfume on a fabric conditioning prill containing nonionic and optionally cationic materials, the prills having a size of 5 to 2000 microns. These prills are picked up by the fabrics during washing and thereafter are melted in a laundry dryer to release the perfume. Sorbitan esters and various fatty acids and their derivatives are suggested as nonionic components of these prills.

DISCLOSURE OF THE INVENTION

We have now surprisingly discovered that a perfume benefit can be obtained by incorporating a perfume in particles comprising a particular range of amines, and that such particles are compatible with detergent active materials usually employed for cleaning surfaces, thereby enabling the cleaning of surfaces and the deposition of perfumes thereon to be carried out in a single step.

Thus according to the invention there is provided a method of cleaning and depositing perfume on a surface, comprising contacting the surface with an aqueous composition containing a perfume and from about 0.05 g per liter to about 8.5 g per liter, based on the volume of the aqueous composition, of a water-soluble detergent active material, with or without a detergency builder, characterised in that the perfume is added to the aqueous composition in the form of from about 0.005 g per liter to about 0.3 g per liter, based on the volume of the aqueous composition of particles having an average size of from about 0.1 micron to about 2000 microns, the particles being an intimate mixture of (a) from about 0.5% to about 50% by weight, based on the weight of the particles, of a perfume component; and (b) from about 50% to about 99.5% by weight, based on the weight of the particles of a matrix comprising at least one water-dispersible amine of the formula $$R—R—R_1R_2$$

where R is an alkyl or alkenyl group having 8 to 22 carbon atoms, $R_1$ is hydrogen or an alkyl or alkenyl group having 1 to 4 carbon atoms, and $R_2$ is hydrogen or an alkyl or alkenyl or amino-alkyl group having 1 to 22 carbon atoms, the matrix containing no added cationic material.

The conditions under which the method of the invention is carried out may vary according to the circumstances, such as whether the surface being treated is a fabric material or a hard surface, the nature of the soil to be removed from the surface the concentration of the aqueous composition, the nature of the detergent active, and the degree of perfume deposition desired. However, the treatment of surfaces with the aqueous composition for a period from 1 to 60 minutes or more and at a temperature of between 20° C. and 90° C. may be found to be suitable.

As will have been seen from the above, the surface to be treated is contacted with the amine/perfume particles and the detergent active material when these materials are in the form of an aqueous composition. This composition may be formed in a variety of methods, such as for example adding to water a solid or concentrated liquid composition containing the detergent active material and the particles.

As a further alternative, the particles may be added to an aqueous medium already containing the detergent active material. The particles may be added to this medium prior to or simultaneously with the contact between the composition and the surface being treated.

To enable the above described methods to be carried out, the present invention further provides (A) a composition containing the detergent active material, from about 0.5% to about 50%, preferably about 0.7% to about 7.0%, by weight of the particles and up to about 20% by weight of water, (B) a liquid composition containing the detergent active material, from about 0.5% to about 50%, preferably about 0.7% to about 2.0%, by weight of the particles and at least 20% by weight of a liquid base, or (C) a composition consisting of the particles, with or without other components.

When these product take the form (A) above, they preferably contain from about 5% to about 85% by weight of the detergent active material, including a detergency builder when present. When the products are in the form (B) above, they may contain at least about 5% by weight of the detergent active material, with or without the detergency builder. It should be noted however, that positive results can be obtained even where the product in the form (A) or (B) above contain less than about 5% by weight of the detergent active material, with or without detergency builder.

Where the composition is in the form of a product having say from about 5% to about 85% by weight of a detergent active material, the aqueous composition for contacting the surface to be treated may be obtained by adding such a product to water at the level of from about 1 g to about 10 g per liter, preferably from about 3 g to about 7 g per liter.

When the products take the form (B) above, the liquid base will normally be primarily water, but may contain other materials, for example, short chain alcohols, buffering agents to provide a desired pH (the pH should not be so low that the amine is converted into a cationic salt form), electrolytes, emulsifiers, colouring materials, perfumes (in addition to the perfume carried on the particles), bactericides, bleaches, bleach precursors, optical brighteners, organic solvents, sequesterants, hydrotropes, viscosity and/or opacity modifying agents, gelling agents, antiredeposition agents, enzymes, abrasives, antifoaming agents, preservatives, and other conventionally used ingredients of detergent compositions. An optical component of the aqueous base is a dispersed fabric conditioning agent in an amount of not more than about 0.5%. When a fabric conditioning agent is present, the weight ratio of particles to fabric conditioning agent is preferably greater than about 100:1. This agent may be a fabric softening agent, selected in particular from quaternary ammonium compounds.

When the products take the form (C) above, they may comprise a composition containing from about 0.5% to about 50%, preferably about 0.7% to about 7.0%, by weight of particles in an aqueous base containing not more than about 5% by weight of a fabric conditioning agent. The fabric conditioning agent, which will usually be a cationic material, may be absent from such compositions. In this case the liquid base will normally be primarily water, but may contain other materials, for example, short chain alcohols, buffering agents to provide a desired pH (the pH should not be so low that the amine is converted into a cationic salt form), electrolytes, emulsifiers, colouring materials, perfumes (in addition to the perfume carried on the particles), bactericides and surface active agents. When a fabric conditioning agent is present, the weight ratio of particles to fabric conditioning agent is preferably greater than about 100:1. The aqueous base may also optionally contain not more than about 5% by weight of a water-soluble detersive surfactant, with or without a detergency builder. Alternatively, when the products take the form (C) above, they may be present in an aqueous base containing above about 50% by weight of the particles. As still further alternatives to product form (C) the particles may be present in a non-aqueous liquid base or mixed with a solid diluent material.

The amines of utility in this invention can be solid, liquid of pasty, and preferably have a solubility in water of less than 1% weight/volume at 20° C. The amines will be dispersible in aqueous media.

The amines used in the present invention are preferably primary amines, that is where $R_1$ and $R_2$ are both hydrogen in the formula $$R—N—R_1R_2,$$

tertiary amines where neither $R_1$ nor $R_2$ is hydrogen, or diamines where $R_2$ is an alkyl amine group.

Where the amine is a diamine, it preferably has the formula $$R—\underset{\displaystyle H}{\underset{|}{N}}—(CH_2)_3—NH_2$$

where R is an alkyl or alkenyl group having 8 to 22 carbon atoms.

The alkyl groups, alkenyl groups and alkyl portion of the amino-alkyl groups may be linear or branched. Preferably, the amine is a primary amine, a tertiary amine or a diamine. Preferred compounds include the following: hardened tallow primary amine, coco primary amine, methyl dihardened tallow tertiary amine, eicosanyl-docosonyl primary amine, methyl dicoco tertiary amine and N-alkyl 1:3 propylene diamines, where the alkyl group is hardened tallow, coco or a $C_{18}/C_{20}$ mixture.

The perfume carrying amine particles preferably have a size of from about 10 to about 500 microns, most preferably from about 50 to about 200 microns. A mixture of different particle sizes may be used. In particular it may be advantageous to use a mixture of relative smaller particles with relatively larger particles with few, if any, particles of intermediate size.

The amount of perfume in the particles should be between about 0.5% to about 50% by weight based on the weight of the particles, preferably between about 10% and about 30%.

The perfume may be selected from any perfumes and any mixtures thereof. Examples of fabric substantive perfumes suitable for use in the present invention are listed in S Arctander, Perfume Flavors and Chemicals, Volumes I and II, published by the Author, Montclair, New Jersey, U.S.A. and the Merck Index, 8th Edition, Merck & Co. Inc., Rahway, New Jersey, U.S.A. Deodorant perfumes such as disclosed in U.S. Pat. No. 4,134,838 may also be used.

In addition to the perfume component and the amine, the particles may contain additionally up to about 49.5% by weight of a non-ionic material, such as sorbitan esters, fatty alcohols and their derivatives.

The matrix will contain no added cationic material. It may be however that the amine used will contain small quantities of cationic material as an impurity. It is preferred that in such circumstances the particles contain no more than about 0.5% cationic material by weight.

The particles of the invention may be prepared by a variety of methods. Thus, for example, the amine and the perfume component are formed into a liquid mixture such as by melting together, which mixture is subsequently transformed into particles of the desired size.

The liquid mixture may be transformed into particles of the desired size by cooling the mixture to a solid, grinding the solid and sieving the resulting particles. Alternatively, the particles may be formed by dispersing the liquid mixture in a liquid medium such as water and optionally separating the particles from the liquid medium.

Alternatively, the liquid mixture may be transformed into particles of the desired size by spray cooling.

As described above the particles may be in a form which includes a detergent active material and optionally a detergency builder. The detergent active material is preferably selected from anionic, nonionic, zwitterionic and amphoteric detergent active materials and mixtures thereof. Thus use of a cationic material as the sole detergent active material is not preferred. Suitable surfactants and builders include those listed in "Surface Active Agents and Detergents", Volumes I and II by Schwartz, Perry & Berch. Preferred detergent active materials include synthetic detergent active materials.

Typical synthetic anionic detergents are the alkyl benzene sulphonates having from 8–16 carbon atoms in the alkyl group, e.g. sodium dodecyl benzene sulphonate; the aliphatic sulphonates, e.g. $C_8$–$C_{18}$ alkane sulphates; the olefin sulphonates having from 10–20 carbon atoms, obtained by reacting an alpha-olefin with gaseous diluted sulphur trioxide and hydrolysing the resulting product; the alkyl sulphates such as tallow alcohol sulphate; and further the sulphation products of ethoxylates and/or propoxylated fatty alcohols, alkyl phenols with 8–15 carbon atoms in the alkyl group, and fatty acid amines, having 1–8 moles of ethoxylene or propoxylene groups.

Typical nonionic detergents are the condensation productions of alkyl phenols having 5–15 carbon atoms in the alkyl group with ethylene oxide, e.g. the reaction product of nonyl phenol with 6–30 ethylene oxide units; the condensation products of higher fatty alcohols, such as tridecyl alcohol and secondary $C_{10}$–$C_{15}$ alcohols, with ethylene oxide, known under the trade name of "Tergitols" (Registered Trade Mark) supplied by Union Carbide, the condensation products of fatty acid amides with 8–15 ethylene oxide units and the condensation products of polypropylene glycol with ethylene oxide.

Also within the scope of this invention are those products which contain soap as a part of the detergent active material or as the sole detergent active material. Suitable soaps include the alkalimetal salt of fatty acids containing between 10 and 24 carbon atoms. Particular examples are the sodium salts of tallow, coconut, palm oil or rapeseed oil fatty acids.

Suitable builders are weakly acid, neutral or alkaline reacting, inorganic or organic compounds, especially inorganic or organic complex-forming substances, e.g. the bicarbonates, carbonates, borates or silicates of the alkalimetals; the alkalimetal ortho-, meta-, pyro- and tripolyphosphates. Another class of suitable builders are the insoluble sodium aluminosilicates as described in Belgian Pat. No. 814,874.

The compositions according to the invention may also include other ingredients conventionally added to detergent compositions, including bleaches, bleach precursors, optical brightening agents, fillers, buffers, antiredeposition agents, preservatives, antifoaming agents, abrasives, thickeners, enzymes, and organic solvents.

Suitable thickeners for the products of the invention include those conventionally used in liquid detergent compositions such as polyethylene oxides, polyethylene glycols, carboxymethyl cellulose, colloidal silica, Carbopol (Registered Trade Mark)—a carboxyvinyl polymer, Natrosol (Registered Trade Mark)—hydroxyethylcellulose and Veegum (Registered Trade Mark)—a modified montmorillonite clay.

Suitable abrasives for use in the products of the invention include calcite, volcanic ash, felspar, quartz, talc and mixtures thereof.

The invention will now be described with reference to the accompanying examples in which parts and percentages are by weight unless otherwise specified.

EXAMPLE 1

19.333 g of hardened tallow primary amine was melted and 0.667 g of a perfume added. An intimate mix was formed by stirring and was then allowed to solidify. The solid was ground in a Moulinex coffee grinder together with dry ice to prevent heat build-up. The particles thus formed were then sieved to give various size fractions, the fraction between 50 μm and 200 μm being selected for use.

2 kg of a mixed synthetic load were washed at 35° C. using 94 g of a conventional detergent composition to which had been added 6 g of particles. A Miele de Luxe 432 front loading automatic washing machine was used with an 18 liter fill of cold Wirral water, giving in liquor:cloth ratio of 9:1.

After the wash cycle had ended fabrics were line dried overnight and assessed for perfume intensity. Comparison was made with a similar load washed in 100 g of detergent to which 0.28 g of perfume had been added by spraying. The results are shown in Table I which quotes the average grading for each formulation on each type of fabric, the grading ranging from 2.0 for strongly detectable perfume to 0.0 for no detectable perfume.

TABLE I

| Fabric | Mean Perfume Intensity | |
|---|---|---|
| | Test Product | Control Product |
| Bulked Nylon | 0.8 | 0 |
| Nylon sheeting | 0.28 | 0 |
| Crimplene | 0.8 | 0 |
| Bulked Acrylic | 0.2 | 0 |

EXAMPLE 2

Example 1 was repeated using 4 g of particles and 96 g detergent. Perfume level in the control product was also reduced to 0.13%.

TABLE II

| Fabric | Mean Perfume Intensity | |
|---|---|---|
| | Test Product | Control Product |
| Bulked Nylon | 0.4 | 0 |
| Nylon sheeting | 0.2 | 0 |
| Crimplene | 0.5 | 0 |
| Bulked Acrylic | 0.2 | 0 |

EXAMPLE 3

Example 1 was repeated using Eicosanyl-Docosanyl primary amine.

TABLE III

| Fabric | Mean Perfume Intensity | |
|---|---|---|
| | Test Product | Control Product |
| Bulked Nylon | 0.6 | 0.1 |
| Nylon sheeting | 0.3 | 0 |
| Crimplene | 0.5 | 0.1 |
| Bulked Acrylic | 0.3 | 0 |

EXAMPLE 4

Particles comprising 95% hardened tallow primary amine and 5% perfume were prepared using a similar method to that given in Example 1. The particles were incorporated at the level of 4% in a conventional detergent composition. The test method was similar to Example 1 and the results were as follows:

TABLE IV

| Fabric | Mean Perfume Intensity |
|---|---|
| Bulked Nylon | 1.0 |
| Nylon sheeting | 0.4 |
| Crimplene | 0.9 |
| Bulked Acrylic | 0.6 |

The conventional detergent composition used in Examples 1 to 4 had the approximate formulation:

| Ingredient | % by weight |
|---|---|
| Anionic detergent active material | 13 |
| Nonionic detergent active material | 7 |
| Sodium tripolyphosphate | 35 |
| Sodium silicate | 5 |
| Sodium sulphate | 26 |
| Water and minor ingredients | balance |

EXAMPLE 5

5 grams of methyl dihardened tallow tertiary amine were heated to 70° C. and 1 gram of perfume was added. After stirring thoroughly, the liquid mixture was dispersed in water at 70° C. with agitation. This formed a first control product —5A.

The process was then repeated with the modification that the water used for dispersing the particles was replaced by a hard surface cleaner base formulation containing 1.5% alkyl benzene sulphonate, 1.5% ether sulphate and 0.2% formalin, balance essentially water. This formed the test product —5B.

A further control product 5C was prepared by adding the same perfume at a rate of 1% by weight to the hard surface cleaner base used for the test product 5B.

These products were then tested as follows. A 6"×6" (approximately 15 cm×15 cm) white glazed tile was supported at 60° to the horizontal. 10 cc of product was poured slowly onto the tile ensuring complete coverage of the surface. Excess product was allowed to drain off for 60 seconds and the tile was then laid flat. An expert panel was then asked to assess each tile for perfume intensity using a scale varying from zero for no detectable perfume to 4 for very strong perfume. The results obtained were averaged and were as follows:

| Product: | 5A | 5B | 5C |
|---|---|---|---|
| Perfume Intensity: | 2.6 | 2.5 | 1.7 |

After 1 hour the tiles were rinsed and assessed again with the following results:

| Product: | 5A | 5B | 5C |
|---|---|---|---|
| Perfume Intensity: | 1.4 | 2.4 | 1.2 |

The tiles were then rinsed and left overnight before a further assessment which gave the following results:

| Product: | 5A | 5B | 5C |
|---|---|---|---|
| Perfume Intensity: | 0.7 | 1.5 | 1.2 |

EXAMPLE 6

Particles were prepared as described in Example 1 above but having the composition 95% amine, 5% perfume and were incorporated into a liquid detergent composition having the following formulation:

| Ingredient | % |
|---|---|
| Dodecyl benzene sulphonic acid | 10 |
| Monoethanolamine | 2.3 |
| Tetrapotassium pyrophosphate | 5 |
| Potassium silicate | 4 |
| Carboxymethylcellulose | 1.3 |
| Potassium xylene sulphonate | 5 |
| Optical brightening agent | 0.1 |
| Distilled coconut oil fatty acid | 8 |
| Caustic potash | 2 |
| Water | balance |

2 kg of a mixed synthetic load were washed at 35° C. using 250 ml of the liquid detergent composition to which had been added 6 g of particles. A top loading automatic washing machine was used with an 18 liter fill of cold Wirral water, giving a liquor:cloth ratio of 9:1.

After the wash cycle had ended fabrics were line dried overnight and assessed for perfume intensity. Comparison was made with a similar load washed using 250 ml of the liquid detergent composition to which the same perfume had been added at the rate of 0.3% by weight. The results were as follows:

TABLE VI

| | Mean Perfume Intensity | |
|---|---|---|
| Fabric | Test Product | Control Product |
| Bulked Nylon | 0.75 | 0.2 |
| Nylon Sheeting | 0.5 | 0 |
| Crimplene | 0.75 | 0.3 |
| Bulked Acrylic | 0.5 | 0.2 |

With the absence of the carboxymethyl cellulose, the above composition would be suitable as a hard surface cleaner.

EXAMPLE 7

Example 6 was repeated using 4 g of particles and 250 ml liquid detergent. Perfume level in the control product was also reduced to 0.13%. A positive preference for the test product was shown on all fabrics.

EXAMPLE 8

Example 6 was repeated using eicosanyl-docosanyl primary amine. A positive preference for the test product was shown on all fabrics.

EXAMPLE 9

Particles comprising 95% hardened tallow primary amine and 5% perfume were prepared using a similar method to that given in Example 6. The particles were incorporated at the level of 4 g per 250 ml of the liquid detergent composition. The test method was similar to Example 1. A positive preference for the test product was shown on all fabrics.

EXAMPLE 10

Particles were prepared as described in Example 1 above but having the composition 95% amine, 5% perfume and were then dispersed in water, with the aid of an ultrasonic agitator, to make up a dispersion containing 5% by weight of the particles.

2 kg of a mixed synthetic load were washed at 35° C. using 94 g of the conventional detergent composition used in Examples 1 to 4. A top loading automatic washing machine was used with an 18 liter fill of cold Wirral water, giving a liquor:cloth ratio of 9:1. 80 ml of the particle dispersion was added to the wash liquor.

After the wash cycle had ended fabrics were line dried overnight and assessed for perfume intensity. Comparison was made with a similar load washed in 100 g of detergent to which 0.2 g of perfume had been added by spraying.

The results were as follows:

TABLE X

| | Mean perfume intensity | |
|---|---|---|
| Fabric | Test Product | Control Product |
| Bulked Nylon | 1.1 | 0.1 |
| Nylon Sheeting | 0.8 | 0.1 |
| Crimplene | 1.3 | 0.3 |
| Bulked Acrylic | 0.4 | 0 |

EXAMPLE 11

Example 10 was repeated using 4 g of particles and 96 g detergent. Perfume level in the control product was also reduced to 0.13%. The results showed a positive preference for the test product on all fabrics tested.

EXAMPLE 12

Example 10 was repeated using eicosanyl-docosanyl primary amine. The results showed a positive preference for the test product on all fabrics tested.

EXAMPLE 13

Particles comprising 95% hardened tallow primary amine and 5% perfume were prepared using a similar method to that given in Example 10. The particles were formed into a 5% dispersion as described in Example 10. The test method was similar to Example 10 except that 96 g of conventional detergent composition and 80 ml of dispersion were used. The results showed a positive preference for the test product on all fabrics tested.

EXAMPLE 14

Using the method described in Example 1, particles were prepared having the following composition:

| Ingredient | % by weight |
|---|---|
| Hardened tallow primary amine | 85 |
| Sorbitan monostearate | 10 |
| Perfume | 5 |

These particles were then tested as described in Example 1, the wash liquor containing 4 g of particles and 96 g of the conventional detergent. The control liquor was formed from 100 g of the conventional detergent to which the same perfume had been added by spraying, to given a concentration of 0.2%.

The results were as follows:

TABLE XIV

| | Mean Perfume Intensity | |
|---|---|---|
| Fabric | Test Product | Control Product |
| Bulked Nylon | 1.1 | 0.4 |
| Nylon Sheeting | 0.6 | 0.2 |
| Crimplene | 0.9 | 0.4 |
| Bulked Acrylic | 0.6 | 0.1 |

EXAMPLE 15

A hard surface scouring powder was prepared according to the following formulation.

| Ingredient | Parts by weight |
|---|---|
| Felspar | 50 |
| Sodium bisulphate | 30 |
| Sodium bicarbonate | 10 |
| Particles | 5 |

The particles consisted of methyl dihardened tallow tertiary amine and perfume in the proportions of 9:2. 2 g of this powder was sprinkled onto a damp ceramic tile 4"×4" and left for 1 hour. After rinsing with 25 ml water, a residual perfume could be detected.

This formulation may be modified by the inclusion of, for example, 2 parts by weight of an anionic surfactant such as DOBS-055.

A suitable perfume for use in the above Examples may have the following approximate formulation:

| | % |
|---|---|
| Amyl Cinnamic Aldehyde | 2.0 |
| Anisic Aldehyde | 1.5 |
| Benzene Acetate | 6.0 |
| Cinnamic Alcohol | 8.0 |
| Hexyl Cinnamic Aldehyde | 4.0 |
| Hydroxycitronellal | 8.0 |
| Indole 10% | 3.0 |
| Iso Eugenol | 1.0 |
| Lilial | 7.0 |
| Linalol | 6.0 |
| Lyral | 7.0 |
| Phenyl Ethyl Alcohol | 18.0 |
| Terpineol | 16.0 |
| Tonalid | 12.0 |
| Vanillin | 0.5 |
| | 100.0 |

I claim:

1. A method of cleaning and depositing perfume on a fabric surface, comprising contacting the fabric surface with an aqueous composition containing a perfume and from about 0.05 g per liter to about 8.5 g per liter, based on the volume of the aqueous composition, of a water-soluble detergent active material, with or without a detergency builder, characterized in that the perfume is added to the aqueous composition in the form of from about 0.005 g per liter to about 0.3 g per liter, based on the volume of the aqueous composition of particles having an average size of from about 0.1 micron to about 2000 microns, the particles being an intimate mixture of (a) from about 0.5% to about 50% by weight, based on the weight of the particles, of a perfume component; and (b) from about 50% to about 99.5% by weight, based on the weight of the particles of a matrix comprising at least one water-dispersible amine of the formula $$R—N—R_1R_2$$

where R is an alkyl or alkenyl group having 8 to 22 carbon atoms, $R_1$ is hydrogen or an alkyl or alkenyl group having 1 to 4 carbon atoms, and $R_2$ is hydrogen or an alkyl or alkenyl or amino-alkyl group having 1 to 22 carbon atoms, the matrix containing no added cationic material.

2. A method according to claim 1, characterized in that the aqueous composition is in contact with the fabric surface for a period of from about 1 minute to about 60 minutes.

3. A method according to claim 1 or 2, characterized in that the aqueous composition is in contact with the fabric surface at a temperature of between about 20° C. and about 90° C.

4. A method according to claim 1 characterized in that the aqueous composition is formed by adding to water a solid composition already containing the detergent active material and the particles.

5. A method according to claim 1 characterized in that the aqueous composition is formed by adding to water a concentrated liquid composition already containing the detergent active material and the particles.

6. A method according to claim 1 characterized in that the aqueous composition is formed by adding the particles to an aqueous medium already containing the detergent active material prior to or simultaneously with the contact between the composition and the fabric surface.

* * * * *